United States Patent
Fathi et al.

(10) Patent No.: US 10,166,219 B2
(45) Date of Patent: Jan. 1, 2019

(54) FORMULATIONS AND METHODS OF MANUFACTURING FORMULATIONS FOR USE IN COLONIC EVACUATION

(71) Applicant: REDHILL BIOPHARMA LTD., Tel-Aviv (IL)

(72) Inventors: Reza Fathi, Hohokus, NJ (US); Patrick Laughlin McLean, Montreal (CA)

(73) Assignee: Redhill Bipharma Ltd., Tel Aviv-Yafo (IL)

( * ) Notice: Subject to any disclaimer, the term of this patent is extended or adjusted under 35 U.S.C. 154(b) by 0 days.

(21) Appl. No.: 14/417,172

(22) PCT Filed: Jul. 26, 2013

(86) PCT No.: PCT/IB2013/001640
§ 371 (c)(1),
(2) Date: Jan. 26, 2015

(87) PCT Pub. No.: WO2014/016671
PCT Pub. Date: Jan. 30, 2014

(65) Prior Publication Data
US 2015/0272937 A1 Oct. 1, 2015

Related U.S. Application Data

(60) Provisional application No. 61/676,608, filed on Jul. 27, 2012.

(51) Int. Cl.
| | |
|---|---|
| *A61K 31/4402* | (2006.01) |
| *A61K 9/28* | (2006.01) |
| *A61K 9/20* | (2006.01) |
| *A61K 31/185* | (2006.01) |
| *A61K 31/375* | (2006.01) |
| *A61K 33/08* | (2006.01) |

(52) U.S. Cl.
CPC ........ *A61K 31/4402* (2013.01); *A61K 9/2009* (2013.01); *A61K 9/2013* (2013.01); *A61K 9/2095* (2013.01); *A61K 9/28* (2013.01); *A61K 9/2893* (2013.01); *A61K 31/185* (2013.01); *A61K 31/375* (2013.01); *A61K 33/08* (2013.01)

(58) Field of Classification Search
None
See application file for complete search history.

(56) References Cited

U.S. PATENT DOCUMENTS

| | | | |
|---|---|---|---|
| 3,459,863 A | 8/1969 | Apelian et al. | |
| 4,186,025 A | 1/1980 | Kang et al. | |
| 4,452,779 A | 6/1984 | Cockerill | |
| 4,766,004 A | 8/1988 | Moskowitz | |
| 4,975,286 A | 12/1990 | Hechter | |
| 5,173,296 A | 12/1992 | Andre et al. | |
| 5,196,205 A | 3/1993 | Borody | |
| 5,213,807 A | 5/1993 | Chemburkar et al. | |
| 5,232,699 A | 8/1993 | Colliopoulos | |
| 5,274,001 A | 12/1993 | Borody | |
| 5,443,826 A | 8/1995 | Borody | |
| 5,476,669 A | 12/1995 | Borody | |
| 5,519,014 A | 5/1996 | Borody | |
| 5,631,022 A * | 5/1997 | Mandel | A61K 9/2846 424/451 |
| 5,843,477 A * | 12/1998 | Alexander | A61K 9/2013 424/464 |
| 5,858,403 A | 1/1999 | Borody et al. | |
| 6,087,386 A | 7/2000 | Chen et al. | |
| 6,103,268 A | 8/2000 | Borody et al. | |
| 6,121,250 A | 9/2000 | Nishiyama et al. | |
| 6,132,767 A * | 10/2000 | Borody | A61K 31/44 424/451 |
| 6,162,464 A | 12/2000 | Jacob et al. | |
| 6,245,740 B1 | 6/2001 | Goldenberg et al. | |
| 6,277,836 B1 | 8/2001 | Borody | |
| 6,284,274 B1 | 9/2001 | Merrill et al. | |
| 6,287,596 B1 * | 9/2001 | Murakami | A61K 9/0056 424/435 |
| 6,303,662 B1 | 10/2001 | Nagahama et al. | |
| 6,426,338 B1 | 7/2002 | Borody | |
| 6,475,510 B1 * | 11/2002 | Venkatesh | A61K 9/0056 424/441 |
| 6,475,518 B1 | 11/2002 | Baumgart et al. | |
| 6,489,317 B1 | 12/2002 | Borody | |
| 6,514,531 B1 | 2/2003 | Alaux et al. | |
| 6,551,632 B2 | 4/2003 | Borody | |
| 6,645,530 B1 | 11/2003 | Borody | |
| 6,774,111 B1 | 8/2004 | Wolf et al. | |
| 6,858,403 B2 | 2/2005 | Han et al. | |
| 6,926,907 B2 | 8/2005 | Plachetka | |
| 6,979,674 B1 | 12/2005 | Goldenberg et al. | |
| 7,763,276 B1 | 7/2010 | Shodai et al. | |
| 7,799,341 B2 | 9/2010 | Porzio et al. | |
| 7,815,956 B2 | 10/2010 | Lee et al. | |
| 7,846,475 B2 | 12/2010 | Shiraishi et al. | |
| 7,993,682 B2 | 8/2011 | Borody et al. | |
| 8,679,549 B2 | 3/2014 | Borody et al. | |

(Continued)

FOREIGN PATENT DOCUMENTS

| | | |
|---|---|---|
| AU | 771576 B2 | 3/2004 |
| CA | 2189418 A1 | 5/1997 |

(Continued)

OTHER PUBLICATIONS

Definition of 'micronize' from http://www.thefreedictionary.com/micronize, downloaded Sep. 16, 2016.*

(Continued)

*Primary Examiner* — Michael P Cohen
(74) *Attorney, Agent, or Firm* — McCarter & English, LLP; Jonathan M. Sparks

(57) ABSTRACT

Formulations and methods of manufacturing formulations for use in colonic evacuation are disclosed herein, in an embodiment, a solid dosage formulation includes an intra-granular fraction intermingled with an extra-granular fraction, wherein the intra-granular fraction includes granules comprising at least one osmotic evacuant agent, at least one antacid, and a first pharmaceutically acceptable excipient component, and wherein the extra-granular fraction includes one or more organic acids, a non-metallic lubricating element, and a second pharmaceutically acceptable excipient component.

5 Claims, 2 Drawing Sheets

(56) References Cited

U.S. PATENT DOCUMENTS

| | | | |
|---|---|---|---|
| 2002/0035075 A1 | 3/2002 | Borody | |
| 2002/0071872 A1 | 6/2002 | McNally et al. | |
| 2003/0092724 A1 | 5/2003 | Kao et al. | |
| 2003/0175336 A1 | 9/2003 | Luber et al. | |
| 2003/0180260 A1 | 9/2003 | Clancy et al. | |
| 2003/0202957 A1 | 10/2003 | Cleveland | |
| 2004/0009961 A1 | 1/2004 | Borody | |
| 2004/0028689 A1 | 2/2004 | Borody | |
| 2004/0038329 A1 | 2/2004 | Clancy et al. | |
| 2004/0259899 A1 | 12/2004 | Sanghvi et al. | |
| 2004/0265378 A1 | 12/2004 | Peng et al. | |
| 2005/0089563 A1 | 4/2005 | Daggy et al. | |
| 2006/0275223 A1 | 12/2006 | Burr | |
| 2007/0057924 A1 | 3/2007 | Prados et al. | |
| 2007/0281905 A1 | 12/2007 | Gripp et al. | |
| 2008/0299197 A1 | 12/2008 | Toneguzzo et al. | |
| 2009/0155363 A1 | 6/2009 | Maibach | |
| 2009/0169622 A1* | 7/2009 | Shukla | A61K 9/2018 424/471 |
| 2009/0258090 A1 | 10/2009 | Cleveland | |
| 2010/0178349 A1 | 7/2010 | Kolter et al. | |
| 2010/0178413 A1 | 7/2010 | Gorris | |
| 2010/0184785 A1 | 7/2010 | Kolter et al. | |
| 2010/0222311 A1 | 9/2010 | Thommes et al. | |
| 2010/0226866 A1 | 9/2010 | Yamashiro et al. | |
| 2010/0233278 A1 | 9/2010 | Ookawa et al. | |
| 2010/0239667 A1 | 9/2010 | Hemmingsen et al. | |
| 2010/0247665 A1 | 9/2010 | Takahashi | |
| 2010/0255307 A1 | 10/2010 | Gonze et al. | |
| 2010/0278930 A1 | 11/2010 | Okumura et al. | |
| 2010/0285164 A1 | 11/2010 | Schaible et al. | |
| 2010/0289164 A1 | 11/2010 | Porzio et al. | |
| 2010/0297031 A1 | 11/2010 | beda Perez et al. | |
| 2011/0218216 A1 | 9/2011 | Vivek et al. | |
| 2011/0223252 A1 | 9/2011 | Borody et al. | |
| 2011/0236475 A1 | 9/2011 | Pasha et al. | |
| 2012/0064133 A1 | 3/2012 | Chauhan et al. | |
| 2012/0156261 A1* | 6/2012 | Fujiwara | A61K 9/0056 424/400 |
| 2012/0183612 A1 | 7/2012 | Brogmann et al. | |
| 2013/0296314 A1 | 11/2013 | Borody et al. | |
| 2015/0056140 A1 | 2/2015 | Borody et al. | |

FOREIGN PATENT DOCUMENTS

| | | | | |
|---|---|---|---|---|
| CA | 2335713 A1 | 1/2001 | | |
| CN | 1288730 A | 3/2001 | | |
| EP | 0397689 A1 | 11/1990 | | |
| EP | 0439453 A4 | 2/1991 | | |
| EP | 0433299 A1 | 6/1991 | | |
| EP | 0554291 A1 | 8/1993 | | |
| EP | 0771562 A2 | 5/1997 | | |
| JP | H06-132767 A | 5/1994 | | |
| JP | H06-340530 A | 12/1994 | | |
| JP | 07242539 | 9/1995 | | |
| JP | 2001-106632 A | 4/2001 | | |
| JP | 2004-210731 A | 7/2004 | | |
| JP | 2005-255595 A | 9/2005 | | |
| JP | 2005-272401 | 10/2005 | | |
| JP | 2007-512336 A | 5/2007 | | |
| JP | 2011-019046 A | 1/2011 | | |
| JP | WO 2011019045 A1 * | 2/2011 | | A61K 9/0056 |
| JP | 2011-068645 A | 4/2011 | | |
| JP | 2011-157346 | 6/2011 | | |
| JP | 2012-079118 A | 4/2012 | | |
| JP | 05306221 B2 | 10/2013 | | |
| NZ | 299685 A | 5/1999 | | |
| NZ | 333493 A | 6/2000 | | |
| RU | 2098100 C1 | 12/1997 | | |
| WO | 8501441 A1 | 4/1985 | | |
| WO | 8605981 A1 | 10/1986 | | |
| WO | 8903219 A1 | 4/1989 | | |
| WO | 8905659 A1 | 6/1989 | | |
| WO | 9001335 A1 | 2/1990 | | |
| WO | 9206690 A1 | 4/1992 | | |
| WO | 1994/18973 A1 | 9/1994 | | |
| WO | 9602236 A1 | 2/1996 | | |
| WO | 9611014 A1 | 4/1996 | | |
| WO | 9843667 A1 | 10/1998 | | |
| WO | 1998043654 A1 | 10/1998 | | |
| WO | 9850043 A1 | 11/1998 | | |
| WO | 1999/009959 A1 | 3/1999 | | |
| WO | 9956749 A1 | 11/1999 | | |
| WO | 0001378 A1 | 1/2000 | | |
| WO | 0167895 A1 | 9/2001 | | |
| WO | 0180852 A1 | 11/2001 | | |
| WO | 0197821 A1 | 12/2001 | | |
| WO | 0203065 | 1/2002 | | |
| WO | 0207741 | 1/2002 | | |
| WO | 2002071872 A2 | 9/2002 | | |
| WO | 03061767 A1 | 7/2003 | | |
| WO | 03074061 A1 | 9/2003 | | |
| WO | 2004070043 A1 | 8/2004 | | |
| WO | 2004100857 A2 | 11/2004 | | |
| WO | 2005051361 A1 | 6/2005 | | |
| WO | 2006118370 A1 | 11/2006 | | |
| WO | 2007057924 A1 | 5/2007 | | |
| WO | 2008021394 A2 | 2/2008 | | |
| WO | 2008027442 A2 | 3/2008 | | |
| WO | 2008141368 A1 | 11/2008 | | |
| WO | WO 2009047633 A2 * | 4/2009 | | A61K 9/009 |
| WO | 2012079118 A1 | 6/2012 | | |
| WO | 2013059881 A1 | 5/2013 | | |
| WO | 2014016671 A2 | 1/2014 | | |
| WO | 2014032108 A1 | 3/2014 | | |

OTHER PUBLICATIONS

Tanja Vehovec, Andrej Gartner, Odon Planinsek, Ales Obreza. Influence of different types of commercially available microcrystalline cellulose on degradation of perindopril erbumine and enalapril maleate in binary mixtures. Acta Pharm. 62 (2012) 515-528.*

Michael G. Herting, Peter Kleinebudde.Roll compaction-dry granulation effect of particle size_int j pharmaceutics 2007 110-118.*

D. Oulahna, F. Cordier, L. Galet, J.A. Dodds. Wet granulation: the effect of shear on granule properties. Powder Technology 130 (2003) 238-246.*

Adrogue, et al., "Hyponatremia", The New England Journal of Medicine, May 25, 2000, vol. 342, No. 21, pp. 1581-1590.

Alternative Sweeteners (O'Brien Nabors, ed. (2001), p. 3).

Altomare, et al., "Colonic explosion during diathermy colotomy. Report of a case", Diseases Colon Rectum Mar.;36(3):291-2 (1993).

Andrews, et al., "'Putting back the bugs': bacterial treatment relieves chronic constipation and symptoms of irritable bowel syndrome", Med J Aust. Nov. 1;159(9):633-4 (1993).

Arieff, et al., "Neurological manifestations and morbidity of hyponatremia; correlation with brain water and electrolytes", Medicine (Baltimore) Mar. ;55(2):121-9 (1976).

Arrigoni et al., "Human gut microbiota does not ferment erythritol", British Journal of Nutrition, 2005, 94:643-646.

Ayus, JC et al., "Treatment of symptomatic hyponatremia and its relation to brain damage. A prospective study," New Engl. J. Med., Nov. 5, 1987, 317(19):1190-5.

Belsey, "Deaths and kidney failures call bowel preparation safety into question", Dec. 17, 2008, pp. 1-5, Norgine.

Bernt et al., "Erythritol: A Review of Biological and Toxicological Studies", Regulatory Toxicology and Pharmacology, 24, S191-S197 (1996).

Bini EJ et al., "Prospective, randomized, single-blind comparison of two preparations for screening flexible sigmoidoscopy", Gastronintest Endosc Aug. 2000; 52(2) 218-22.

Booth, A.N. et al., "Effects of Prolonged Ingestion of Xylose on Rats", In the Journal of Nutrition, 1953, pp. 347-355.

Bornet et al., "Gastrointestinal Response and Plasma and Urine Determinations in Human Subjects Given Erythritol", Regulatory Toxicology and Pharmacology 24, S296-S302 (1996).

(56) References Cited

OTHER PUBLICATIONS

Borody et al., "A Phase II, Comparative, Single-blinded, Randomised Study to Evaluate the Efficacy and Safety of Hypertonic Solution Combined with PicoPrep™ Capsules Compared with PicoPrep™ Capsules Alone, Standard Glycoprep™ and Standard PicoPrep™ as a Bowel Preparation" Clinical Study Report, Version 1 (2006).
Borody et al., "Electrolyte Purgative", Australian Provisional application No. PS0887 dated Mar. 4, 2002.
Borody, "Flora Power-fecal bacteria cure chronic C. difficile diarrhea", Am J Gastroenterol., 95(11):3028-9 (2000).
Borody, "Helicobacter pylori eradication failure—'salvage' therapies needed", Ital J Gastroenterol Hepatol., 30(4):375-7 (1998).
Borody, et al., "Apparent reversal of early gastric mucosal atrophy after triple therapy for Helicobacter pylori", Am J Gastroenterol., 88(8):1266-68 (1993).
Borody, et al., "Bacteriotherapy using fecal flora: toying with human motions", J Clin Gastroenterol., 38(6):475-83 (2004).
Borody, et al., "Bowel-flora alteration: a potential cure for inflammatory bowel disease and irritable bowel syndrome?", Med J Aust., 150(10):604 (1989).
Borody, et al., "Eradication therapies for Helicobacter pylori", J Gastroenterol. 33 Supp 10:53-6 (1998).
Borody, et al., "Helicobacter pylori eradication with doxycycline-metronidazole-bismuth subcitrate triple therapy", Scand J Gastroenterol., 27(4):281-4 (1992).
Borody, et al., "Lactoferrin: milking ulcers?", Dig Liver Dis., 35(10):691-3. (2003).
Borody, et al., "Treatment of ulcerative colitis using fecal bacteriotherapy", J Clin Gastroenterol., 17(1):42-7 (2003).
Borody, et al., "Use of high efficacy, lower dose triple therapy to reduce side effects of eradicating Helicobacter pylori", Am J Gastroenterol., 89(1):33-8 (1994).
Borody, Thomas J., Giaconda Limited Newsletter, Issue 2, Dec. 2006.
Borody, Thomas J., News Release Giaconda Limited, Giaconda announces positive phase II data for PICOCONDA. Presented at Australian Gastroenterology Week, Oct. 10, 2006.
Burger, S.A., et al., "A Mannitol-Bisacodyl Regimen for Radiological Visualization of the Colon," SA Medical Journal, Jul. 14, 1979. Retrieved from the Internet: http://archive.samj.org.za/1979%20VOL%20LVI%20Jul-Dec/Articles/01%20July/2.9%20A%20MANNITOL-BISACODYL%20REGIMEN%20FOR%20RADIOLOGICAL%20VISUALIZATION%20OF%20THE%20COLON,%20S.A.Burger,%20D.Spies.pdf.
Campbell, Karen, "Why is Everyone Going on About Childhood Overweight and What Can We Do About It?", Nutridate, vol. 18, No. 1, Mar. 2007, pp. 1-9.
Carulli, N. et al., "Absorption of Lactulose in Man", Digestion, 1972, 6:139-145.
Chapman, M.A.S. et al., "Antibacterial activity of bowel-cleansing agents: implications of antibacteroides activity of senna", British Journal of Surgery, 1995, 82, 1053.
Clark, C. Graham et al., "Methods of Cultivation of Luminal Parasitic Protists of Clinical Importance", Clinical Microbiology Reviews, Jul. 2002, vol. 15, No. 3, pp. 329-341.
Cohen CD, Keuneke C, Schiemann U, Schroppel B, Siegert S, Rascher W, Gross M, Schlondorff D, "Hyponatraemia as a complication of colonoscopy", Lancer Jan. 27;357(9252):282-3 (2001).
Corazziari, E. et. al., "Small Volume Isosmotic Polyethylene Glycol Electrolyte Balanced Solution (PMF-100) in Treatment of Chronic Nonorganic Constipation", Digestive Diseases and Sciences. vol. 41, No. 8, Aug. 1996, pp. 1636-1642.
de Boer, et al., "Treatment failures and secondary resistance to antibiotics. A growing concern in Helicobacter pylori therapy", Dig Liver Dis., 32(8):673-5 (2000).
Defang et al, "In Vitro and in Vivo Evaluation of Two Extended Release Preparations of Combination Metformin and Glipizide." Drug Development and Industrial Pharmacy (2005) 31(7):677-85 (abstract).

Dennison, Barbara A., "Fruit Juice Consumption by Infants and Children: A Review", Journal of the American College of Nutrition, vol. 15, No. 5, 4S-11S (1996).
Derwent Abstract Accession No. 93-408836, JP 05306221 A (Horii Yakunhin Kogyo KK) "Intestinal rinse soln. contains magnesium citrate, sodium chloride, potassium hydroxide and sugar", Nov. 19, 1993 Abstract Only.
Derwent Abstract Accession No. 98-375395, RU 2098100 C1 (Maksimova et al.), "Intestinal rinse soln. contains magnesium citrate, sodium chloride, potassium hydroxide and sugar" Dec. 10, 1997 Abstract Only.
Duthie, "Do you really know what you are drinking?", Nutri Dat 18(1): 5-8 (2007).
Dye, "The inadequacy of the usual determinative tests for the identification of Xanthomonas SPP," New Zealand Journal of Science, 5(4):393-416 (1962).
El-Gendy, Nashwa et al., "Dry powdered aerosols of diatrizoic acid nanoparticle agglomerates as a lung contrast agent", International Journal of Pharmaceutics, 391 (2010) pp. 305-312.
Ellegard, L. et al., "Inulin and oligofructose do not influence the absorption of cholesterol, or the excretion of cholesterol, Ca, Mg, Zn, Fe, or bile acids but increases energy excretion in ileostomy subjects", European Journal of Clinical Nutrition, 1997, 51, 1-5.
Extended European Search Report, Application No. EP11848334, dated Mar. 14, 2014.
Fincher, et al., "A comparison of bowel preparations for flexible sigmoidoscopy: oral magnesium citrate combined with oral bisacodyl, one hypertonic phosphate enema, or two hypertonic phosphate enemas", Am. J. Gastroenterol., 94(8):2122-7 (1999).
Fraser, et al., "Sex differences result in increased morbidity from hyponatremia in female rats", Am J Physiol., 256(4 Pt 2):R880-5 (1989).
Hiele, Martin et al., "Metabolism of erythritol in humans: comparison with glucose and lactitol", British Journal of Nutrition, 1993, 69, 169-176.
Horii, Yakuhin Kogyo KK, "Intestinal rinse soln. contains magnesium citrate, sodium chloride, potassium hydroxide and sugar", Derwent Abstract, Accession C93-181899, 1993.
Hoy et al., "Sodium Picosulfate/Magnesium Citrate: A Review of its Use as a Colorectal Cleanser", Drugs, 69 (1): 123-136, Jan. 1, 2009.
Huang et al, "Once-daily Propranolol Extended-Release Tablet Dosage Form: Formulation Design and in Vitro/in Vivo Investigation." European Journal of Pharmaceutics and Biopharmaceutics (2004) 58(3):607-14 (abstract).
International Preliminary Report on Patentability and Written Opinion, International Application No. PCT/AU2011/001609, dated Dec. 13, 2011.
International Preliminary Report on Patentability and Written Opinion, International Application No. PCT/AU2013/000973, dated Mar. 3, 2015.
International Preliminary Report on Patentability and Written Opinion, International Application No. PCT/IB2013/001640, dated Jan. 27, 2015.
International Preliminary Report on Patentability, International Application No. PCT/AU2012/001315, dated Oct. 27, 2012.
International Search Report, International Application No. PCT/AU03/00257, dated Apr. 24, 2003.
International Search Report, International Application No. PCT/AU2011/001609, dated Jan. 17, 2012.
International Search Report, International Application No. PCT/AU2012/001315, dated Oct. 27, 2012.
International Search Report, International Application No. PCT/AU2013/000973, dated Aug. 29, 2013.
International Search Report, International Application No. PCT/IB2013/001640, dated Jan. 14, 2014.
IPCS Inchem Home, "Toxicological Evaluation of Some Antimicrobials, Antioxidants, Emulsifiers, Stabilizers, Flour-Treatment Agents, Acids and Base", FAO Nutrition Meetings Reports, 40A, B, C, WHO/Food Add./67.29, 1965.
Izzo et al., "The osmotic and intrinsic mechanisms of the pharmacological laxative action of oral high doses of magnesium sulphate. Importance of he release of digestive polypeptides and nitric oxide", Magnes Res 1996, June, 9(2): 133-8.

(56) References Cited

OTHER PUBLICATIONS

JP 07242539, Fukahori, A. et al., "Compositions having laxative effect, used in treatment of constipation comprise organic acid, sugar alcohol, and optional calcium salts", 1995, Derwent Abstract, pp. 1-7.

Kawakami, JP 05-306221, Intestinal Canal Irrigation Solution Composition and Intestinal Canal Irrigation Solution, English Translation (H4-132042), Nelles Translations, 7 pages.

Kharidia et al, "The Activity of a Small Lytic Peptide PTP-7 on Staphylococcus aureus Biofilms." The Journal of Microbiology (2011) 49(4):663-8 (abstract).

Kienzle-Horn et al., "Comparison of bisacodyl and sodium picosulphate in the treatment of chronic constipation" Current Medical Research and Opinions (2007) 23(4):691-699.

Kuksal et al, "Formulation and in vitro, in vivo evaluation of extended-release matrix tablet of Zidovudine: Influence of combination of hydrophilic and hydrophobic matrix formers" AAPS PharmSciTech. Mar. 2006; 7(1): E1-E9.

Lai, Edwin J. et al., "The Boston bowel preparation scale: a valid and reliable instrument for colonscopy-oriented research," Gastrointestinal Endoscopy, vol. 69, No. 3, Part 2 of 2, 2009, pp. 620-625.

Liacouras, Piccoli, "Whole-bowel irrigation as an adjunct to the treatment of chronic, relasping Clostridium difficile colitis", J Clin Gastroenterol, Apr. 22, 1996 (3):186-9 (Abstract).

Maksimovais, "Physiological saline-based irrigant for use in eye surgery—contains solutions of calcium, magnesium and potassium chloride(s), phosphate buffer, glucose solution and asorbic acid solution", Derwent Accession No. C98-113774, 1997.

Melton, et al., "Volume regulatory loss of Na, Cl, and K from rat brain during acute hyponatremia", Am J Physiol., 252(4 Pt 2):F661-9 (1987).

Munro, Erythritol: An Interpretive Summary of Biochemical, Metabolic, Toxicological and Clinical Data, Food and Chemical Toxicology, 36 (1998) 1139-1174.

Noda et al., "Metabolism and Disposition of Erythritol after Oral Administration to Rats", In the Journal of Nutrition, 1992, pp. 1266-1272.

Norgine Pty Ltd, "Deaths and kidney failures call bowel preparation safety into question" United Kingdom, Dec. 17, 2008.

O'Brien Nabors, Lyn, "Alternative Sweeteners", Third Edition, Revised and Expanded, 2001, pp. 1-3.

Oku, et al "Laxative Threshold of Sugar Alcohol Erythritol in Human Subjects" Nutrition Research (1996) 16(4):577-589.

Parente et al., "Bowel preparation before colonoscopy in the era of mass screening of colo-rectal cancer: A practical approach", ScienceDirect, Digestive and Liver Disease 41 (2009) 87-95.

PHARMGKB, "Pharmacology and Interactions", Mannitol Data Sheet, Download from http://www.pharmgkb.org/do/serve?objId=PA450320&objCls=drug, Jun. 1, 2010.

Pimentel et al., "Methane, a gas produced by enteric bacteria, slows intestinal transit and augments small intestinal contractile activity" Am. J. Physiol. Gastrointest. Liver Physiol. (2006) 290:G1089-G1095.

Remington Parmaceutical Sciences (16th edition, Osol, ed, 1980) p. 873.

Rider, et al, "Treatment of Acute and Chronic Constipation with Bisoxatin Acetate and Bisacodyl: Double-Blind Crossover Study" Current Therapeutic Research (1971) 13(6)386-392.

Ross, et al., Differential Permeability of the Proximal and Distal Rabbit Small Bowel, Journal of Clinical Investigation, vol. 51, Sep. 1972.

Schiller, "Review Article: the therapy of constipation", Ailment Pharmacol Ther, 2001, 15:749-763.

Sharma et al., "Randomized, Controlled Comparison of Two Forms of Preparation for Screening Flexible Sigmoidoscopy", The American Journal of Gastroenterology, vol. 92, No. 5, 1997, pp. 809-811.

Song et al., "Recent advances in the biological production of mannitol", Appl Microbiol Biotechnol (2009) 84:55-62.

Stahl et al., "The Salt-Optimization Process—First Phase" Handbook of Pharmaceutical Salts: Properties, Selection and Use (2008) pp. 167-169.

Swinyard, Ewarl, "Diuretic Drugs", Chapter 49, Remington's, Pharmaceutical Sciences, 1980, p. 873.

Tetzloff et al., "Tolerance to Subchronic, High-Dose Ingestion of Erythriol in Human Volunteers", Regulatory Toxicology and Pharmacology, 24: S286-S295 (1996).

Tsuneyuki, O., et al., "Laxative threshold of sugar alcohol erythritol in human subjects," Nutrition Research, 16(4):577-589, Apr. 1996.

Winawer et al., "Colorectal Cancer Screening and Surveillance: Clinical Guidelines and Rationale—Update Based on New Evidence", Gastroenterology, 2003, 124:544-560.

Windholz, M. (Editor), Sodium Chlorite, The Merck Index, Ninth Edition, 1976, p. 1111.

Written Opinion, International Application No. PCT/AU2011/001609, dated Dec. 13, 2011.

Written Opinion, International Application No. PCT/AU2012/001315, dated Oct. 27, 2012.

Written Opinion, International Application No. PCT/AU2013/000973, dated Nov. 4, 2013.

Written Opinion, International Application No. PCT/IB2013/001640, dated Jan. 14, 2014.

Khan et al., "Metal Ion and Metal Chelate Catalyzed Oxidation of Ascorbic Acid by Molecular Oxygen. I. Cupric and Ferric Ion Catalyzed Oxidation", Journal of the American Chemical Society, 89(16):4176-4185, 1967.

Lindberg et al., Optimization of Disintegration Time and Crushing Strength of a Tablet Formulation. Drug Development and Industrial Pharmacy. 1985;11(4):931-943.

Rahman et al., Effect of Mode of Addition of Disintegrants on Dissolution of Model Drug from Wet Granulation Tablets. International Journal of Pharma Sciences and Research. 2011;2(2):84-92.

\* cited by examiner

FORMULATIONS AND METHODS OF MANUFACTURING FORMULATIONS FOR USE IN COLONIC EVACUATION

CROSS-REFERENCE AND CLAIM OF PRIORITY

This application is a national phase application under 35 U.S.C. § 371 of PCT International Application No. PCT/IB2013/001640, filed Jul. 26, 2013, which claims the benefit of U.S. provisional patent application Ser. No. 61/676,608, filed Jul. 27, 2012, the entire contents of each of which are hereby incorporated by reference.

BACKGROUND

The advent of colonoscopy brought with it the need for a simplified, routine bowel cleansing protocol or product to achieve a clean colonic mucosa required to detect even small lesions or abnormalities in the bowel. Similar requirements exist for colonic surgery.

SUMMARY

Formulations and methods of manufacturing formulations for use in colonic evacuation are disclosed herein.

According to aspects illustrated herein, there is disclosed a solid dosage formulation that includes an intra-granular fraction intermingled with an extra-granular fraction, wherein the intra-granular fraction includes granules comprising at least one osmotic evacuant agent, at least one antacid, and a first pharmaceutically acceptable excipient component, and wherein the extra-granular fraction includes one or more organic acids, a non-metallic lubricating element, and a second pharmaceutically acceptable excipient component.

According to aspects illustrated herein, there is disclosed a method of evacuating a colon of a patient that includes orally administering to the patient, within a 24-hour time frame, between 25 and 30 tablets with a liquid, wherein each of the tablets includes an intra-granular fraction intermingled with an extra-granular fraction, wherein the intra-granular fraction includes granules comprising sodium picosulfate, magnesium oxide, simethicone and a first pharmaceutically acceptable excipient component, wherein the extra-granular fraction includes ascorbic acid and a second pharmaceutically acceptable excipient component, and wherein all the tablets combined yield a total dose of about 30 mg sodium picosulfate, about 7 g of magnesium oxide, about 15 g of ascorbic acid, and about 100 mg of simethicone. In an embodiment, the formulation requires a minimum ingestion of fluid while avoiding side effects of fluid shifts. In an embodiment, the formulation has an optimal drug release profile and suitable stability to provide adequate shelf life.

According to aspects illustrated herein, there is disclosed a method of manufacturing a solid dosage formulation that includes (i) wet granulating at least one osmotic evacuant agent, at least one antacid, and a first pharmaceutically acceptable excipient component to form an intra-granular fraction; (ii) blending the intra-granular fraction obtained from step (i) with elements of an extra-granular fraction comprising one or more organic acids, a non-metallic lubricating element, and a second pharmaceutically acceptable excipient component; and (iii) compressing the blend obtained from step (ii) into tablets.

BRIEF DESCRIPTION OF THE DRAWINGS

The presently disclosed embodiments will be further explained with reference to the attached drawings.

Figure 1:
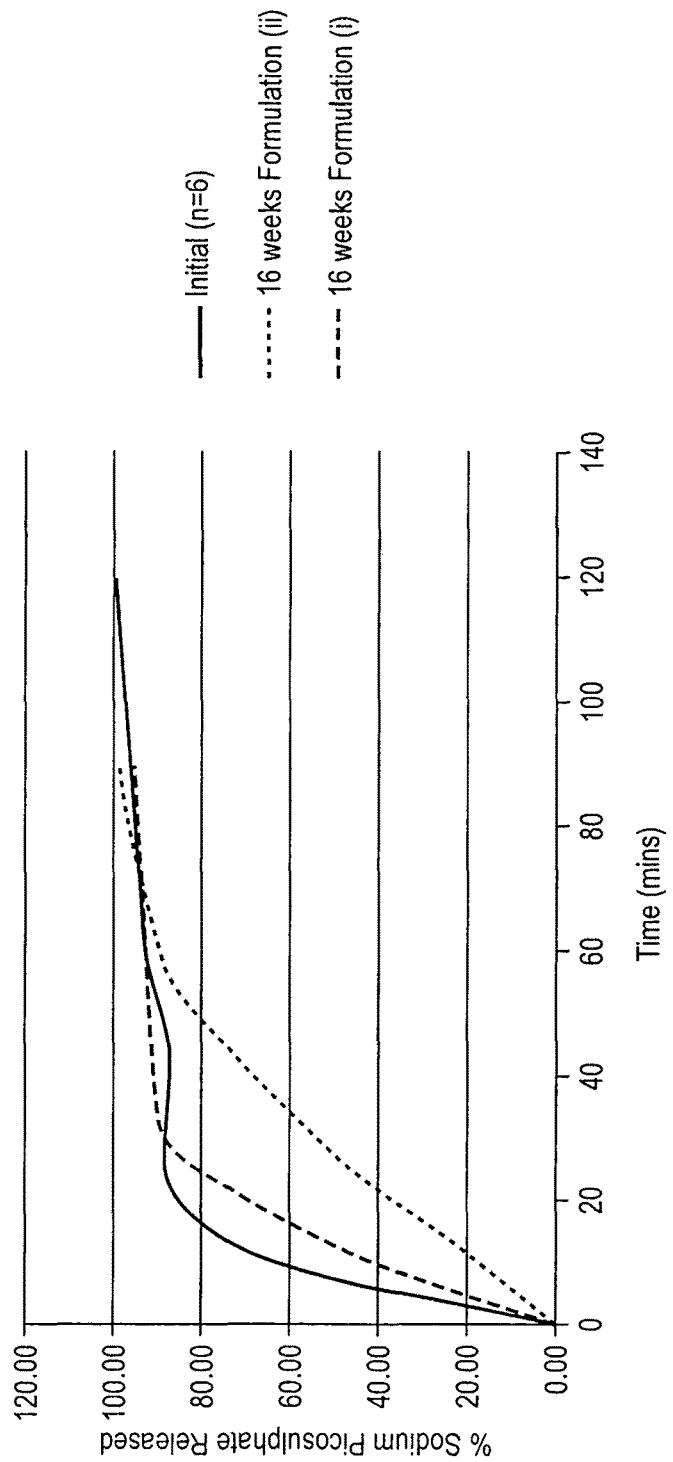
FIG. 1 is a graph showing the release of sodium picosulfate over time from formulations of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Formulations and methods of manufacturing formulations for use in colonic evacuation are disclosed herein. In an embodiment, a solid dosage formulation includes an intra-granular fraction intermingled with an extra-granular fraction, wherein the intra-granular fraction includes granules comprising at least one osmotic evacuant agent, at least one antacid, and a first pharmaceutically acceptable excipient component, and wherein the extra-granular fraction includes one or more organic acids, a non-metallic lubricating element, and a second pharmaceutically acceptable excipient component.

As used herein, the term "intra-granular fraction" refers to those components of a formulation of the present invention that are within granules.

As used herein, the term "extra-granular fraction" refers to those components of a formulation of the present invention that are outside of the granules. During manufacturing, the extra-granular fraction includes the ingredients that are added to the intra-granular fraction post-drying.

In an embodiment, the intra-granular fraction (i.e. granules) may for example comprise up to 50% of the total weight of the formulation, e.g. from 30% to 50% by weight of the formulation. The at least one osmotic evacuant agent component of the intra-granular fraction may for example comprise up to 1% of the total weight of the formulation. The at least one antacid component of the intra-granular fraction may for example comprise up to 20% of the total weight of the formulation. The first pharmaceutically acceptable excipient component of the intra-granular fraction may for example comprise up to 30% of the total weight of the formulation. The granules of the intra-granular fraction may, for example, have a size of from 25 microns to 1000 microns. The granules of the intra-granular fraction may, for example, have an average size of from 150 microns to 300 microns.

In an embodiment, the extra-granular fraction may for example comprise up to 50% of the total weight of the formulation. The one or more organic acids of the extra-granular fraction may for example comprise up to 40% of the total weight of the formulation. The non-metallic lubricating element of the extra-granular fraction may for example comprise up to 3% of the total weight of the formulation. The second pharmaceutically acceptable excipient component of the extra-granular fraction may for example comprise up to 10% of the total weight of the formulation.

Suitable osmotic evacuant agents include, but are not limited to, sulfate based laxatives and phosphate based laxatives. Examples of sulfate based laxatives include, but are not limited to, sodium picosulfate, sodium sulfate and magnesium sulfate. A mixture of two or more sulfate based laxatives may be used. Examples of phosphate based laxatives include, but are not limited to, sodium dihydrogen phosphate, disodium hydrogen phosphate, sodium biphosphate, sodium acid pyrophosphate, and/or mixtures thereof.

The osmotic evacuant agent may further comprise an antacid selected from the group consisting of magnesium oxide, calcium carbonate, magnesium alginate, magnesium hydroxide, magnesium carbonate, magnesium citrate, magnesium aspartate, and magnesium trisilicate. In an embodiment, the antacid is magnesium oxide. In one embodiment, the osmotic evacuant agent comprises a mixture of sodium picosulfate and magnesium oxide.

In a further embodiment, the sodium picosulfate comprises micronized sodium picosulfate.

The formulation of the present disclosure may be a tablet. For example the tablet may be a compressed tablet, a coated tablet or an exploding tablet. Alternatively, the formulation may comprise a capsule. Examples include a coated capsule or an exploding capsule; a lozenge; or a pill.

The formulation may have a delayed release profile, a slow release profile or a controlled release profile of one or more of the at least one osmotic evacuant agent; the one or more organic acids; or the at least one excipient including a non-metallic lubricating agent.

To achieve a delayed release of one or more components of the pharmaceutical composition, it may be formulated with a coating as noted above. Further, the delayed release of one or more of the components may be achieved by other formulation methods including multiple layers or compartments of the solid oral dosage form.

Suitable organic acids include, but are not limited to, ascorbic acid, citric acid, tartaric acid, mixtures of citric acid and ascorbic acid, and mixtures of tartaric acid in combination with ascorbic acid and/or citric acid.

Typically, the lubricating agent of the formulation comprises a fatty acid ester. For example, the lubricating agent may comprise glyceryl behenate. In an embodiment, Compritol® 888ATO is used as the glyceryl behenate. In another embodiment, the fatty acid ester may result from one or more of the following fatty acids: caprylic acid, capric acid, lauric acid, myristic acid, palmitic acid, stearic acid, lignoceric acid, oleic acid, linoleic acid, erucic acid, linoleic acid, or coconut oil.

The formulation may further include a number of other excipients including a diluent selected from one or a mixture of any one or more of the following: mannitol, lactose monohydrate, microcrystalline cellulose (e.g. sold under the trade name Avicel® PH 101), or sorbitol.

The formulation may further include a binder agent. For example the formulation may include polyvinyl pyrrolidone (PVP), including PVP K30; hydroxypropylcellulose, or polyethylene glycol (PEG), including PEG 10000 or PEG 4000.

Typically, the formulation also includes a stabilizing agent. Suitable stabilizing agents include, but are not limited to, sodium metabisulfite, sodium bisulphite and sodium sulfite.

A disintegrant may also be included in the formulation and may include cross linked povidone (crospovidone). Alternatively sodium starch glycolate (SSG) may be used as a disintegrant.

An anti-foaming agent may also be included in the formulation. Suitable anti-foaming agents include, but are not limited to, polydimethylsiloxane, hydrated silica gel, and mixtures of polydimethylsiloxane and hydrated silica gel. In one embodiment the anti-foaming agent is simethicone. A further example of an anti-foaming agent is dimethicone.

An anti-adherent element may also be included in the formulation for the intra-granular fraction and for the extra-granular fraction and may be the same or different and may comprise one or more (known) substances or compounds which (in appropriate amounts) are capable of reducing the stickiness of the composition or formulation, for example, inhibiting adherence to metal surfaces. Suitable anti-adherent type materials include, but are not limited to, talc and silicon-containing compounds such as colloidal silicon dioxide (e.g. sold under the trade name Aerosil®) as well as mixtures thereof.

Generally, the formulation may be orally administered with any liquid suitable for ingestion. Preferably, water, mineral water, glucose-free mineral water, glucose-free cordial or glucose-free soft drink are used. The volume of liquid consumed with the formulation varies from 250 mL to 2,000 mL, for example, 250 mL to 1,500 mL or 500 mL to 1,500 mL or 2,000 mL.

Generally, the formulation is orally administered to a patient over a period of time. The formulation is usually prepared as a number of tablets or capsules which are taken over a period of time.

A typical total dose of the osmotic evacuant agent is in the range of from 1 to 100 mg, preferably 5 to 50 mg, preferably 10 to 40 mg, more preferably 30 mg. In one embodiment, the evacuant agent in such a dosage regimen comprises a sulfate based laxative.

A typical example of a treatment regimen involves the preparation of the formulation into approximately 30 tablets or capsules. Approximately 5 tablets or capsules are ingested with approximately one glass of liquid over a period of 1 second to 20 minutes, typically 5 seconds to 5 minutes, typically 10 seconds to 3 minutes, typically 30 seconds to 15 minutes, typically 15 minutes to 20 minutes, typically 1 minute to 10 minutes, more typically 1 minute to 6 minutes. A further 5 tablets or capsules are ingested with approximately one glass of liquid over 10 seconds to 20 minutes, typically 30 seconds to 15 minutes, or 15 minutes to 20 minutes, typically 1 minute to 10 minutes, more typically 1 minute to 6 minutes after approximately 20 minutes to 2.5 hours, typically 25 minutes to 1 hour, more typically 30 to 40 minutes. This regimen is repeated until all the tablets or capsules have been ingested.

A typical example of a treatment regimen of the invention involves the preparation of the formulation into approximately 5 to 40 tablets or capsules. Approximately one fifth of the tablets or capsules are ingested with approximately one glass of liquid over a period of 1 second to 20 minutes, typically 5 seconds to 5 minutes, typically 10 seconds to 3 minutes, typically 30 seconds to 15 minutes, typically 15 minutes to 20 minutes, typically 1 minute to 10 minutes, more typically 1 minute to 6 minutes. A further one fifth of the tablets or capsules are ingested with approximately one glass of liquid over 10 seconds to 20 minutes, typically 30 seconds to 15 minutes, or 15 minutes to 20 minutes, typically 1 minute to 10 minutes, more typically 1 minute to 6 minutes after approximately 20 minutes to 2.5 hours, typically 25 minutes to 1 hour, more typically 30 to 40 minutes. This regimen is repeated until all the tablets or capsules have been ingested.

Generally, the typical examples of the treatment regimen take 2 to 15 hours, for example, 2 to 12 hours or 2.5 to 15 hours, preferably 2.5 to 6.5 hours, more preferably 2 to 4.5 hours, even more typically 2 to 3.5 hours.

If the treatment regimen is administered in two parts, there is usually a difference of 4 to 16 hours, typically 4 to 12 hours, preferably 4 to 8 hours, more preferably 4 to 6 hours, between the administration of the first treatment regimen and the administration of the second treatment regimen.

The formulations of the present disclosure are also useful in the treatment of certain gastrointestinal conditions such as small bowel bacterial overgrowth and irritable bowel syndrome as well as useful in treating acute or chronic bacterial bowel infections, for example, infection of the bowel with one or more bacteria including *Campylobacter jejuni, Yersinia enterocolitica, Clostridium difficile, Cryptosporidium isospora belli*. The formulation of the present disclosure can also be used in the treatment of fungal or viral infections in the bowel. The osmotic colonic evacuant of the present invention can also be used in the treatment of chronic inflammatory bowel disease such as Crohn's disease or ulcerative colitis.

In one embodiment the formulation may be produced by granulation. The granulation steps may include dry granulation. Alternatively, the granulation steps may include wet granulation. The formulation includes an intra-granular fraction intermingled with an extra-granular fraction. Typically, the at least one osmotic evacuant agent is granulated with one or more excipients and dried to provide an initial granulation mixture. As a separate step, the one or more organic acid is added to the initial granulation mixture to provide a second mixture. As a final step one or more lubricating agents may be added to the second mixture and the formulation mixed for a pre-determined time period.

The formulation may further comprise one or more layers or compartments. In this embodiment it is envisaged that the at least one osmotic evacuant agent includes a compound having metallic ions and wherein the compound having metallic ions is in a different layer or compartment to that containing the one or more organic acid. For example, if the at least one osmotic evacuant agent includes magnesium oxide, the formulation in solid dosage form would include the magnesium oxide in a separate layer or compartment to the acid. In an embodiment where ascorbic acid is present, such a physical separation would significantly reduce the degradation of the acid in the presence of metallic cations.

The solid dosage formulation may comprise a coating layer to relatively delay dissolution beyond the mouth of a patient. A suitable coating agent may include PVA, TiO2, talc, lecithin (soy), and xantham gum (e.g. sold under the name Opadry® AMB White). Further, the coating agent may include PVA, polyethylene glycol and talc (sold under the trade name Opadry® II Clear). The coating layer may further include methyl methacrylate and diethylaminoethyl methacrylate copolymer. An example of suitable lubricants is sold under the trade name Kollicoat® and the various compositions are herein incorporated as examples.

EXAMPLES

With aspects of the present formulations and methods now being generally described, these will be more readily understood by reference to the following examples, which are included merely for purposes of illustration of certain features and embodiments of the present formulations and methods and are not intended to be limiting. Table 1 lists the actives and excipients used in the formulation development studies:

TABLE 1

| Material | Trade Name | Supplier |
| --- | --- | --- |
| Sodium picosulfate (micronized) | N/A | Cambrex |
| Simethicone LVA | N/A | Dow Corning |
| Simethicone for DC | N/A | SPI Pharma |
| Magnesium oxide (heavy) | N/A | Intermag |
| Magnesium oxide (granular) | N/A | Intermag |
| EC coated Ascorbic acid | N/A | 3051-WO1 |
| FC coated Ascorbic acid | N/A | DSM |
| Sodium ascorbate | N/A | Sigma |
| Mannitol (Pearlitol 200 SD) | Pearlitol ® 200SD | Roquette |
| Lactose monohydrate | Pharmatose ® 200M | DMV Fonterra |
| Microcrystalline Cellulose | Avicel ® PH-101 | FMC |
| Microcrystalline Cellulose | Avicel ® PH-102 | FMC |
| Polyvinyl Pyrrolidone K30 | Povidone K30 | BASF |
| Prosolv Easy Tab | | JRS Pharma |
| Hydroxypropylcellulose (HPC) | Klucel ® | Hercules |
| Polyethylene glycol 10000 | N/A | Clariant |
| Polyethylene glycol 4000 | N/A | Prolabo |
| Citric acid anhydrous | N/A | Sigma |
| Tartaric acid | N/A | Fluka |
| Sodium metabisulphite (97%) | N/A | Alfa Aesar |
| Sodium bisulphite (sodium hydrosulphite) | N/A | Alfa Aesar |
| Sodium sulphite | N/A | Alfa Aesar |
| Sodium starch glycollate | Explotab ® | JRS |
| Crospovidone | Polyplasdone ® XL | ISP |
| Magnesium Stearate | N/A | Riedel de Haen |
| Glyceryl behenate | Compritol ® 888 ATO | Gattefossé |
| Silicon Dioxide | Aerosil ® 200 | In house sample |
| HMPC Capsules | N/A | Qualicaps |
| Sodium Lauryl Sulphate | N/A | VWR |
| OPADRY AMB white | N/A | Colourcon |
| OPADRY II clear | N/A | Colourcon |

Example 1

Formulation Studies

Formulation studies were undertaken to compare powder formulations in capsules (size 0) and tableting studies. Granulation was used as a densification method and various methods such as aqueous, melt and dry granulation were studied. Various changes were made to the formulations and different prototypes prepared. Both the powder blends and the granulated formulations were examined for tapped density, powder flow, compressibility index, moisture content and sieve analysis.

Dry Powder Blends

Powder blends were prepared as follows: the required amounts of active and excipients were dispensed into suitable containers. To a high shear mixer the following were added in order: ascorbic acid (half), MgO (halt), SSG, sodium picosulfate, binder, simethicone, MgO (half) and ascorbic acid (half). This mixture was mixed for a pre-determined time period, for example, 2 mins at high speed with the mixer shaken/tilted occasionally. Small portions of the powder blend were transferred into a jacketed vessel that was preheated at a selected temperature, for example, 62° C.-65° C. and mixed with a spatula until granules were formed. This was repeated until all the powder blend was granulated. The granules were emptied into wide opened glass beakers and cooled at room temperature overnight. The granules were sieved, weighed and the extra-granular excipients added accordingly. The resulting mixture was agitated and stirred for a pre-determined time period, for example 10 mins. Lubricant was then added and mixed for a pre-determined time period, for example 1 minute.

Melt Granulation

Melt agglomeration is a process by which the solid fine particles are bound together into agglomerates, by agitation, kneading, and layering, in the presence of a molten binding liquid. Dry agglomerates are obtained as the molten binding liquid solidifies on cooling. The main advantages of the procedure are that neither solvent nor water is used in this process, hence the procedure is suitable for molecules that dissociates in aqueous media. Fewer processing steps are needed thus time consuming drying steps are eliminated. Formulations were prepared using a jacketed vessel and two different hydrophilic meltable binders, PEG 10,000 and PEG 4,000. Both meltable binders were milled down using a Kenwood mixer as they were relatively large flakes. Two methods were used to add the binder to the formulation:

Method A:

The binder was added directly to the formulation blends and mixed either using the low shear mixer (Kenwood) or the Turbula mixer.

Powder blends were prepared as follows:
1. The required amounts of active and excipients were dispensed into suitable containers.
2. The active was then sandwiched between diluent in a high shear mixer (Kenwood) by adding in the following order: ascorbic acid (half), MgO (half), SSG, sodium picosulfate, binder, simethicone, MgO (half) and ascorbic acid (half).
3. Mixed for 2 mins at high speed with the mixer shaken/tilted occasionally.
4. Transfer small portions (40 g) of the powder blend in the jacketed vessel preheated at 62-65° C. mixed with a spatula until granules were formed. This was repeated until all the powder blend was granulated.
5. Emptied the granules in wide opened glass beakers and leave to cool down at room temperature overnight.
6. Sieve, weight and add accordingly the extra-granular excipients.
7. Mix with Turbula mixer for 10 mins at 49 rpm.
8. Add magnesium stearate and mix just for 1 minute at 49 rpm.

Method B:

A single batch of the formulation prepared by hot melt granulation was also prepared by pre-melting the binder in the jacketed vessel, to investigate the effect of the method of the preparation on the flow properties. The other steps were as above.

As the theoretical fill weight for the melt granulation formulation was higher compared to the dry powder blend, it was estimated that formulations with a tapped density of 1.25-1.32 g/ml will be required in order to be filled into size 0 or 0el. Several formulations were prepared where various factors were investigated such as: using different amount and grades of PEG, using different grades of MgO, different mixing time and different temperature for mixing.

As the amount of the meltable binder increased, no significant change in the tapped density was observed. The highest tapped density value achieved was for a formulation containing 10% w/w PEG10,000 mixed for 30 mins at 65° C. Percentages lower than 10% for PEG, might give slightly higher tapped density values to aid packing. Formulations prepared with the same composition but using different grade of MgO (granular and heavy) indicated that a higher tapped density value can be achieved when granular MgO is used. The Carr's index was between 13-21%, suggesting that good powder flow was achieved. Formulations prepared with different grade of PEG, gave similar values for the tapped density, but still not high enough to ensure the target fill weight could be achieved. Generally all formulations prepared by hot melt granulation had lower tapped density values than the desired formulation, suggesting that it will be difficult to achieve the target fill weight into a size 0 or 0el.

Using caplet tooling, a tablet was created. Various settings of the tabletting machine were used but the smallest tablets prepared by hand were ~1.1 g (target weigh was 860 mg/caplet for 30 units required). Hence it was decided to increase the fill weight of the caplets and reduce the number of caplets required to deliver the target doses (20 caplets rather than 30). A number of caplets were manually produced using two different machine setting to obtain different hardness and the data indicated that the caplets were uniform in terms of weight and general dimensions. The softer caplets showed a longer disintegration time of just under 14 mins. Hence more super disintegrant will be required in this formulation to reduce the disintegration time. Further, the caplets showed also a change in colour (mottling effect) which might be due to the degradation of one of the excipients during granulation or tabletting.

Direct Compression

A formulation blend was prepared by adding ProSolv® Easy Tab (a commercially available blend containing, MCC 102, $SiO_2$, SSG and sodium stearyl fumarate) and simethicone suitable for direct compression. The theoretical fill weight was increased to allow dosing 24 caplets. The formulation was further optimized by adding 5% Klucel®, Mannitol and increased level of super disintegrant. Caplets were produced in automatic mode using three different settings and results for the tabletting indicated that caplets produced by direct compression were uniform and the hardness varies from 25N (softest) to 78N (hardest), the increase in SSG level reduced the disintegration time, and that all 3 types of caplets, with various hardness's, failed the friability test. The results indicated that this formulation blend was not suitable for tabletting.

Dry Granulation (Slugging)

In a dry granulation process the powder mixture is compressed without the use of heat and solvent. The two basic procedures are to form a compact of material by compression and then to mill the compact to obtain a granules. Two methods are used for dry granulation and slugging is one of these methods. The more widely used method is roller compaction. Granulation by slugging is the process of compressing dry powder of tablet formulation with a tablet press having a die cavity large enough in diameter to fill quickly. Once slugs are produced they are reduced to appropriate granule size for final compression by grinding and sieving or milling. Powder blends were prepared as follows:
1. Required amount of active and excipients were dispensed into suitable containers.
2. Preblend the simethicone with a portion of Avicel® in the high shear blender (Kenwood)
3. The active was then sandwiched between the excipients in Turbula mixer by adding in the following order: ascorbic acid (half), MgO (half), SSG, sodium picosulfate, binder, simethicone/Avicel® mixture from point 2, MgO (half) and ascorbic acid (half)
4. Mix for 10 mins using the Turbula mixer at 49 rpm.
5. Tablet the formulation blend using 15 mm round flat tooling in order to obtain soft tablets.
6. Mill the soft tablets in the mortar and pestles and sieve through 600 μm sieve. Record the weight.
7. Add in sandwich mode the granules and the extra granular excipients and mix in Turbula mixer for 10 mins at 49 rpm.
8. Add magnesium stearate and mix for a further 1 minute at 49 rpm.

Preliminary data on the formulations indicated that a higher amount of super disintegrant was required to aid disintegration. Hence a new formulation was manufactured where:
Simethicone suspension was replaced with simethicone for direct compression to improve uniformity within the blend,
Avicel® PH-101 was replaced with grade PH-102 to improve potentially the compressibility of the powder and add increased the level of super disintegrant.

A formulation was tabletted in automatic mode using 2 different machine settings in order to produce caplets with 1000 mg theoretical weight (weight corresponding to 30 caplets required for dosing). Caplets with increased weight were also produced at the hardest setting possible, in order to reduce the number of caplets required for administration. Data indicated that:
Caplets produced were generally uniform and the hardness varied from 61 N (softest) to 99 N (hardest).
Friability tests were performed for all types of caplets. Both sets of caplets failed the friability test as caplets split into halves (delaminate/capping) suggesting that the excipients do not bind well together in the formulations investigated).

These indicated that different types and higher levels of excipients suitable for direct compression were needed it to aid tableting.

Wet Granulation

Wet granulation involves addition of a liquid solution (with or without binder) to powders, to form a wet mass. Typically granules are formed by binding the powder together with help from an adhesive. In the pre-mix step the powders to be granulated and powdered binder are added and mixed prior to the introduction of the aqueous solution. In the wet massing step the components are massed to a predetermined end point. In the drying step the wet mass is dried to a predetermined end point, commonly measured with a test called the loss on drying (LOD). The dried granules are then milled to reduce the size of any caked material into a standardized particle size distribution. Then the final blend is prepared by adding the extra granular excipients, and lubricated. Blends were prepared as follows:
1. Required amount of active and excipients were dispensed into suitable containers.
2. Weight deionized water into a separate container.
3. Place all excipients into the high shear mixer and mix them at high speed for 5 mins.
4. Add water gradually and mix continuously until granules were formed.
5. Empty the granules and spread thinly in a tray to dry out either at room temperature (over week-end) or in the oven at ~35-40° C.
6. Perform moisture analysis to assess the end time point for drying.
7. Sieve, weigh, add accordingly the extra granular excipients and mix with Turbula mixer for 10 mins at 49 rpm. (sieve analysis was performed for optimized formulations only)
8. Add magnesium stearate and mix just for 1 minute at 49 rpm.

A formulation was tabletted manually using a 19×9 mm caplet tooling using three different machine settings to generate caplets with different hardness'. The caplets were uniform in weight and physical characterization but had a high disintegration time (more than 15 mins for the softest caplets). This suggested that the level of the super disintegrant needed to be increased to reduce the disintegration time to under 15 mins. Thus, a new formulation blend was prepared where lactose was replaced with mannitol (due to a potential Maillard reaction between NH group from sodium picosulfate and lactose) and super disintegrant (SSG) level was increased to improve hardness and disintegration time. Caplets were produced in automatic mode using three different machine setting and the results are shown below:
Caplets produced were uniform in terms of weight and the hardness varies from 64 N (softest) to 133 N (hardest).
The increase in SSG level reduced the disintegration time.
The softest caplets, failed the friability test. The other 2 settings produce caplets which passed both the disintegration and friability test. Conventional compressed tablets that losses less than 0.5% to 1% of weight are considered acceptable.

Following the success in producing caplets (with 1275 mg theoretical weight required for 30 caplets) with good disintegration, friability and dissolution profile, new caplets were produced with increased theoretical weight (1593 mg) in order to reduce the number of caplets administered (24 caplets/patient). Caplets that passed both disintegration and friability test were prepared. However the caplets were thicker and potentially difficult to swallow.

Example 2

Stability Studies

Two formulations were prepared and analyzed, one dry powder blend filled into size 0el and one formulation prepared by wet granulation as a caplet.

For the Initial Time Point:
The assay, content uniformity, and dissolution results were variable for the dry blend filled into capsule indicating a non-homogeneous blend of the sodium picosulfate. The water content observed for the capsule formulation was higher than for the tablet formulation.

The assay, content uniformity, and dissolution results were consistent for the wet granulation tablet indicating a homogeneous blend of the sodium picosulfate. Also no impurities were observed in this formulation.

For T=1 Months
The assay, content uniformity, and dissolution results remained variable for the dry blend capsule indicating a non-homogeneous blend of the sodium picosulfate. The water content observed had increased in comparison to the initial analysis, and remained higher than for the tablet formulation.

The assay, content uniformity, and dissolution results were consistent, and comparable to the initial data, for the wet granulation tablet indicating a homogeneous blend of the sodium picosulfate. The water content observed was consistent in comparison to the initial analysis, and remained to be lower than for the capsule formulation. Also, there was an increase in impurities seen.

Both formulations changed colour at 40° C./75% RH even at T=2 weeks indicating degradation process. It was believed that the browning effect was due to the ascorbic acid degradation in presence of high moisture and on heat.

To confirm which combination of ingredients lead to changing colour of the formulations, several binary and tertiary mixtures of sodium picosulfate, ascorbic acid and citric acid were prepare with the individual excipients present in the formulation. Additional components were added to investigate the effect of adding some stabilizers to the original formulation to prevent browning effect. Samples were also place into three types of containers, closed, opened, and in DUMA bottles with desiccant, to study the effect of the moisture ingress.

Example 3

Excipient Compatibility Studies

Excipient compatibility studies with all excipients against Na picosulfate and ascorbic acid were carried out. Antioxidants like Na meta-bisulphite, Na bisulphite and Na sulphite were added. Further, the study was carried out to determine if citric acid helped stabilize the colour change of ascorbic acid. Samples were assessed at 1 week, 2 weeks, 4 weeks and at 8 weeks. Table 2 lists the study parameters:

TABLE 2

| | Excipients | | |
|---|---|---|---|
| | Na Picosulfate 10:1 | Ascorbic acid 10:1 | Citric Acid 10:1 |
| Mannitol | ✓ | ✓ | ✓ |
| Magnesium Oxide powder | ✓ | ✓ | ✓ |
| Simethicone for DC powder | ✓ | ✓ | ✓ |
| Ascorbic acid | ✓ | | ✓ |
| Na starch glycollate | ✓ | ✓ | ✓ |
| PVP K30 | ✓ | ✓ | ✓ |
| HPMC | ✓ | ✓ | ✓ |
| Avicel PH101 | ✓ | ✓ | ✓ |
| Aerosil | ✓ | ✓ | ✓ |
| Mg stearate | ✓ | ✓ | ✓ |
| Compritol 888ATO | ✓ | ✓ | ✓ |
| Na meta-bisulphite | ✓ | ✓ | ✓ |
| Na bisulphite | ✓ | ✓ | ✓ |
| Na sulphite | ✓ | ✓ | ✓ |
| Citric acid | ✓ | ✓ | |
| Na Picosulfate | | ✓ | ✓ |

Tertiary Mixtures with Components (250 mg MgO+500 mg AA+25 mg Sulphites (or 100 mg Acids)
MgO+ascorbic acid+Na meta-sulphite
MgO+ascorbic acid+Na bisulphite
MgO+ascorbic acid+Na sulphite
MgO+ascorbic acid+citric acid
MgO+ascorbic acid+tartaric acid
MgO+sodium ascorbate+Na meta-sulphite
MgO+sodium ascorbate+Na bisulphite
MgO+sodium ascorbate+Na sulphite
MgO+sodium ascorbate+citric acid
MgO+sodium ascorbate+tartaric acid
Quaternary Mixtures with Components ((250 mg MgO+500 mg AA+20 NaP+25 mg Sulphites (or 100 mg Acids)
MgO+Na picosulfate+ascorbic acid+Na meta-sulphite
MgO+Na picosulfate+ascorbic acid+Na bisulphite
MgO+Na picosulfate+ascorbic acid+Na sulphite
MgO+Na picosulfate+ascorbic acid+citric acid
MgO+Na Picosulfate+ascorbic acid+tartaric acid Binary, tertiary and quaternary mixtures of the API and excipients at various ratios were prepared as follows:
1. Weigh approximately required amount of excipient into a weighing boat.
2. Add approximately half of the excipient quantity into a container.
3. Weigh the API/ascorbic acid/citric acid into the container.
4. Manually mix the blend and with the aid of the micro-spatula break-up any agglomerates.
5. Blend the mixture in a Turbula mixer for 15 minutes at 49 rpm.
6. After mixing all samples were assumed to be homogenous, and were dispensed in suitable containers, then placed on stability storage. Pull times: 1, 2, 4 and 8 weeks.

Excipients compatibility study showed that:
Up to 8 weeks, binary mixtures with ascorbic acid changed colour in presence of excipients and stabilizers containing metallic cations. Some changes were noted also in opened containers also.
No changes in colour was observed for binary and tertiary mixtures when kept in DUMA bottles with desiccant cap suggesting that the final product will have to be protected from moisture ingress.

The excipient compatibility study of ascorbic acid with various excipients indicated that ascorbic acid degrades in the presence of metallic cations (such as: $Cu^{2+}$, $Fe^{3+}$, $Zn^{2+}$). As a result, two changes were made to the formulation blend prepared by wet granulation. Firstly, the sodium starch glycollate was replaced with crospovidone XL, and secondly the magnesium stearate was replaced with Compritol 888ATO. Also the Avicel® PH101 was added split 50/50 intra-granular and extra-granular.

Example 4

Optimization of Wet Granulated Formulation Blend

Further optimization studies were carried out for the wet granulated formulation. To reduce ascorbic acid degradation in the presence of metallic cations, some excipients of the formulation containing metallic cations were replaced with non-metallic excipients. Additionally, and with a view to further minimising ascorbic acid degradation, the steps of granulation were modified and the effects of having a coating reviewed.

Three wet granulation formulations were prepared, where Avicel was added i) intra granular, ii) split intra granular and extra granular and iii) extra granular only. All three batches were prepared as follows:
1. Required amount of active and excipients were dispensed into suitable containers.
2. Weight deionized water into a separate container.
3. Place all excipients into the high shear mixer and mix at high speed for 2 mins.
4. Add water gradually and mix continuously until granules were formed. Record the amount of water used and the mixing time.
5. Empty the granules and spread thinly in a tray to dry out either at room temperature (over week-end) or in the oven at ~35-40° C.
6. Perform moisture analysis to assess the end time point for drying.
7. Collect approximately 100 g of the dry granules and perform sieve analysis.
8. Add accordingly the extra granular excipients and mix with Turbula mixer for 10 rains at 49 rpm.

Sieve Analysis Indicated that:

Formulations containing Avicel as intra-granular excipient (100 or 50%) have a smaller median particle diameter compared to the formulation containing no Avicel intra-granular. This suggests that the formulations containing some Avicel intra-granular are more suitable for further studies, as bigger granules might lead to segregation caused by particle size difference between materials in a bulk blend.

Powder flow properties indicated that all three formulations prepared had good powder flow properties.

Example 5

Formulations

Formulation A was prepared by wet granulation at ~1.5 kg scale, yielding enough batch to prepare between 25 and 30 tablets, wherein all the tablets combined yield a total dose of about 30 mg sodium picosulfate, about 7 g of magnesium oxide, about 15 g of ascorbic acid, and about 100 mg of simethicone. Table 3 lists the components of Formulation A:

TABLE 3

|  | Weight (mg) | Weight (mg) | Wt/unit | % w/w | Weight (g) |
|---|---|---|---|---|---|
| Intra-granular Components |  |  |  |  |  |
| Mannitol | 7200 | 7200.00 | 240.00 | 18.82 | 301.17 |
| Magnesium Oxide granules | 7000 | 7000.00 | 233.33 | 18.30 | 292.81 |
| Sodium picosulfate (micronized) | 30 | 31.17 | 1.04 | 0.08 | 1.30 |
| Simethicone for DC | 100 | 147.71 | 4.92 | 0.39 | 6.18 |
| Crospovidone | 940 | 940.00 | 31.33 | 2.46 | 39.32 |
| PVP K30 | 1800 | 1800.00 | 60.00 | 4.71 | 75.29 |
| Microcrystalline Cellulose-50% (Avicel® PH101) | 1893 | 1893.00 | 63.10 | 4.95 | 79.18 |
| The above constituents were granulated and dried then sieved and the following added accordingly: |  |  |  |  |  |
| Extra-granular Components |  |  |  |  |  |
| Microcrystalline Cellulose-50% (Avicel® PH101) | 1893 | 1893.00 | 63.10 | 4.95 | 79.18 |
| Ascorbic acid | 15000 | 15151.52 | 505.05 | 39.61 | 633.78 |
| Crospovidone | 940 | 940.00 | 31.33 | 2.46 | 39.32 |
| Aerosil® | 105 | 105.00 | 3.50 | 0.27 | 4.39 |
| The above constituents were granulated and dried then sieved and the following added accordingly: |  |  |  |  |  |
| Compritol® 888ATO | 1149 | 1149.00 | 38.30 | 3.00 | 48.06 |
| TOTAL | 38157 | 38250.40 | 1275.01 | 100.00 | 1600.00 |

Median Particle Diameter for the intra-granular granules of Formulation A was 289 microns.

Formulation B was prepared by wet granulation at ~1.5 kg scale, yielding enough batch to prepare between 25 and 30 tablets, wherein all the tablets combined yield a total dose of about 30 mg sodium picosulfate, about 7 g of magnesium oxide, about 15 g of ascorbic acid, and about 100 mg of simethicone. Table 4 lists the components of Formulation B:

TABLE 4

|  | Weight (mg) | Weight (mg) | Wt/unit | % w/w | Weight (g) |
|---|---|---|---|---|---|
| Intra-granular Components |  |  |  |  |  |
| Mannitol | 6314.5 | 6314.50 | 210.48 | 16.51 | 247.63 |
| Magnesium Oxide granules | 7000 | 7000.00 | 233.33 | 18.30 | 274.51 |
| Sodium picosulfate (micronized) | 30 | 31.17 | 1.04 | 0.08 | 1.22 |
| Simethicone for DC | 100 | 147.71 | 4.92 | 0.39 | 5.79 |
| Crospovidone | 1925 | 1925.00 | 64.17 | 5.03 | 75.49 |
| PVP K30 | 1100 | 1100.00 | 36.67 | 2.88 | 43.14 |
| Microcrystalline Cellulose-50% (Avicel ® PH101) | 1700 | 1700.00 | 56.67 | 4.44 | 66.67 |
| The above constituents were granulated and dried then sieved and the following added accordingly: |  |  |  |  |  |
| Extra-granular Components |  |  |  |  |  |
| Microcrystalline Cellulose-50% (Avicel ® PH101) | 1700 | 1700.00 | 56.67 | 4.44 | 66.67 |
| Ascorbic acid | 15000 | 15151.52 | 505.05 | 39.61 | 594.18 |
| Crospovidone | 1925 | 1925.00 | 64.17 | 5.03 | 75.49 |
| Aerosil ® | 105 | 105.00 | 3.50 | 0.27 | 4.12 |
| The above constituents were granulated and dried then sieved and the following added accordingly: |  |  |  |  |  |
| Compritol ® 888ATO | 1150 | 1150.00 | 38.33 | 3.01 | 45.10 |
| TOTAL | 38157 | 38249.90 | 1275.00 | 100.00 | 1500.00 |

Median Particle Diameter for the intra-granular granules of Formulation B was 175 microns.

The blend and content uniformity of uncoated batches of Formulation A were found to be consistent and to a high standard, see Table 5 below.

TABLE 5

| Uncoated Tablets | | |
|---|---|---|
| | Blend uniformity | Content uniformity |
| Batch | % Assay | % Assay |
| Min | 83.41 | 86.74 |
| Max | 108.61 | 100.42 |
| Avg | 90.71 | 91.44 |
| S.D | 7.95 | 4.62 |
| % RSD | 8.77 | 5.05 |

The appearances of the tablets were initially smooth, plain colour on all sides and free from any spots. Further studies to compare uncoated tablets of Formulation A with coated tablets were performed. Tablet characteristics of uncoated batches of Formulation A are provided below in Table 6:

TABLE 6

| Uncoated Tablets | | | | | | | |
|---|---|---|---|---|---|---|---|
| Tablet | Weight (g) | Length (mm) | Thickness (mm) | Width (mm) | Hardness (N) | Friability test | Disintegration time |
| Average | 1.28 | 19.24 | 6.83 | 9.12 | 106.40 | PASSED (0.16%) | PASSED (5-6 MIN) |
| Std | 0.01 | 0.09 | 0.06 | 0.01 | 2.15 |  |  |
| % RSD | 0.74 | 0.49 | 0.86 | 0.15 | 2.02 |  |  |

Further samples of Formulation A using different coatings and coating parameters were prepared. Examples of the coatings used in the studies are listed in Table 7:

TABLE 7

| Coating Type | Chemical Composition of Coating layer | Coating Solution Concentration | Coating parameters | Coating Weight gain |
|---|---|---|---|---|
| Opadry® AMB White | PVA, TiO2, talc, lecithin (soy), Xanthan gum | 20% w/w | Time 37 min Temp 46-50° C. | 4.85% w/w |
| Opadry® II Clear | PVA, polyethylene glycol, talc | 20% w/w | Time 19 min Temp 46-50° C. | 4.62% w/w |

The coated formulations of Formulation A were:

Coated Formulation (i)=Formulation A coated using Opadry® AMB White and stored at 25° C./60% RH;

Coated Formulation (ii)=Formulation A coated using Opadry® AMB White and stored at 40° C./75% RH Coated Formulation (iii)=Formulation A coated using Opadry® II clear at 40° C./75% M.

A stability study of the coated tablets was undertaken and the following results observed:

Appearance of the Tablet Initially and after 4 Weeks.

A) Initial appearance:
  Coated Formulation (i)
    oblong, smooth, plain white colour on both sides, free from any spots
  Coated Formulation (ii)
    oblong, smooth, plain white colour on both sides, free from any spots
  Coated Formulation (iii)
    not tested
B) Appearance at 4 weeks:
  Coated Formulation (i)
    oblong, smooth, plain white colour on both sides, free from any spots
  Coated Formulation (ii)
    oblong, smooth, plain white colour on both sides, free from any spots
  Coated Formulation (iii)
    oblong, smooth, pale yellow colour on both sides Moisture Content of the Tablets after 4 Weeks.

Table 8 shows the % Water Content by Karl Fischer (T=4 weeks) for three different batches of each of coated formulations (i), (ii) and (iii).

TABLE 8

| Batch | Coated Formulation (i) | Coated Formulation (ii) | Coated Formulation (iii) |
|---|---|---|---|
| 1 | 6.01 | 7.08 | 6.15 |
| 2 | 6.52 | 6.87 | 6.11 |
| 3 | 5.94 | 6.96 | 6.34 |
| Mean | 6.15 | 6.97 | 6.20 |

Table 9 shows the Moisture Content by Karl Fischer (comparative data of mean % water content of each coated formulation at T=0, 2 weeks, 4 weeks, 8 weeks, 12 weeks and 16 weeks).

TABLE 9

| Formulation | Initial | 2 weeks | 4 weeks | 8 weeks | 12 weeks | 16 weeks |
|---|---|---|---|---|---|---|
| (i) | 7.67 | 7.78 | 6.15 | 6.60 | 6.48 | 6.49 |
| (ii) | 7.67 | 7.60 | 6.97 | 6.59 | 6.76 | 7.68 |

Drug Release

Formulations (i) and (ii) were further tested for drug release of the sodium picosulfate over time. Table 10 lists the dissolution parameters

TABLE 10

| Dissolution Parameters | |
|---|---|
| Media | 1% SLS (Sodium Lauryl Sulphate) in de-ionised water |
| RPM | 100 (150 from 60 to 90 minutes) |
| Bath temperature | 37.5 ± 0.5° C. |
| Volume | 500 ml |
| Apparatus | USP-II (paddle) |
| Time points | 0, 10, 20, 30, 45, 60 and 90 mins |

Figure 2:
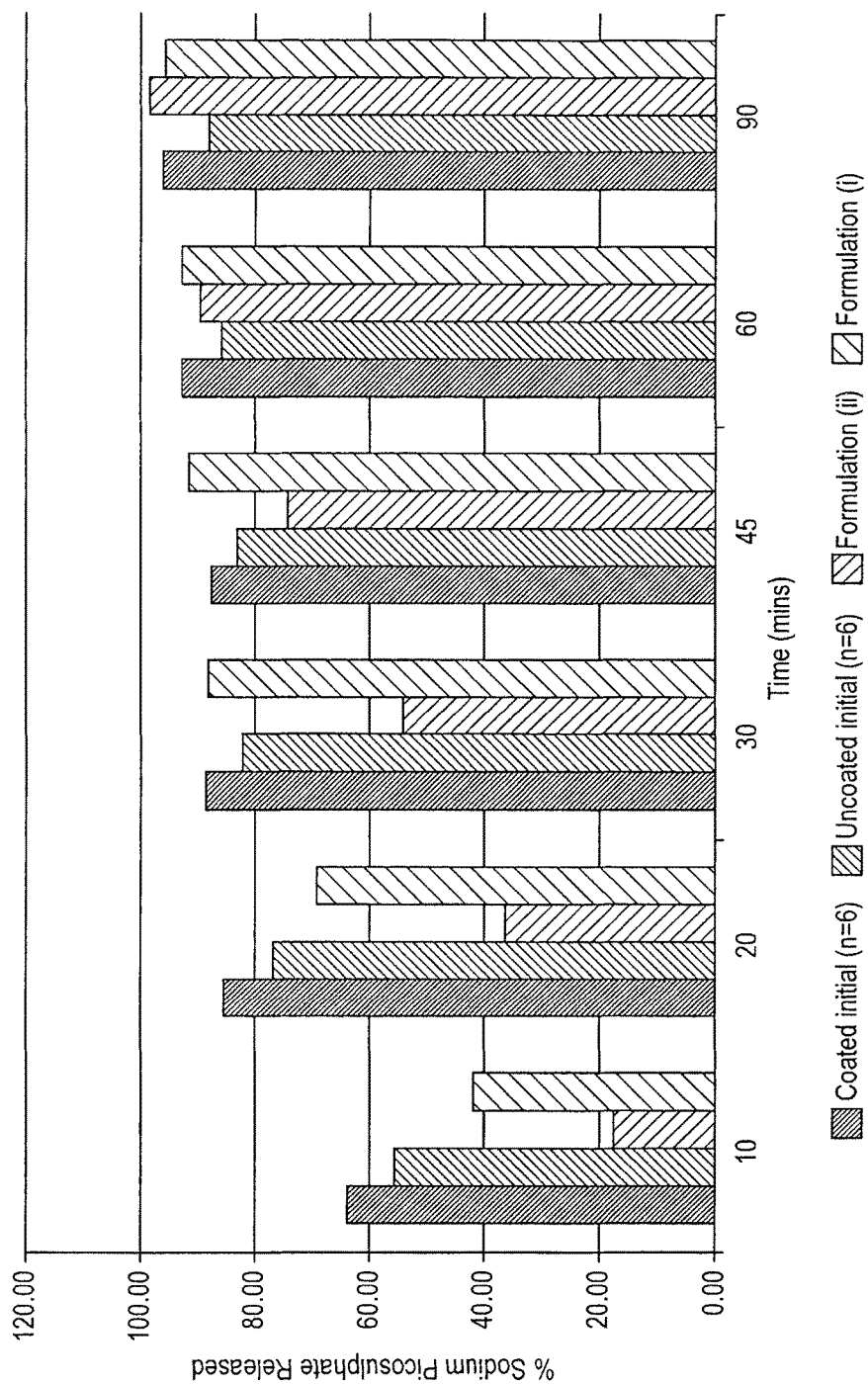
FIG. 2 is a bar graph showing the release of sodium picosulfate over time from formulations of the present disclosure.

Percentage drug release of sodium picosulfate in formulations (i) and (ii) over time is shown in FIG. 1 and FIG. 2.

Summary

At 16 weeks, there was no change in the physical appearance of the tablets of formulation (ii) compared to initial samples. There was also no significant variation observed in the moisture level from the initial samples to the 16 week samples.

The dissolution data showed that 80% drug release was achieved after 30 minutes for the tablet of formulation (i). A delay in the release of sodium picosulfate was observed for formulation (ii), that is, when kept at 40° C. at 75% RH.

The formulation of this disclosure provided a stable tablet form with no signs of degradation at 16 weeks and which delivered an optimal drug release profile.

All patents, patent applications, and published references cited herein are hereby incorporated by reference in their entirety. It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive. Various presently unforeseen or unanticipated alternatives, modifications, variations, or improvements therein may be subsequently made by those skilled in the art which are also intended to be encompassed by the following claims.

What is claimed is:

1. A coated tablet, comprising: an intra-granular fraction combined with an extra-granular fraction, and a coating layer,
  wherein the intra-granular fraction includes granules comprising micronized sodium picosulfate, microcrystalline cellulose, magnesium oxide, and crospovidone, and wherein the intra-granular fractions excludes sodium starch glycolate,
  wherein the extra-granular fraction includes one or more organic acids, microcrystalline cellulose, and crospovidone, and wherein the extra-granular fraction excludes sodium starch glycolate and magnesium stearate, wherein the organic acid is one of ascorbic acid, citric acid, tartaric acid, or combinations thereof, and wherein the coating layer delays dissolution beyond the mouth of a patient.

2. The coated tablet of claim 1 wherein the intra-granular fraction comprises about 50% of the total weight of the formulation, and wherein the extra-granular fraction comprises about 50% of the total weight of the formulation.

3. The coated tablet of claim 1 wherein the at least one organic acid is ascorbic acid.

4. The coated tablet of claim 1, wherein the coated tablet shows no signs of degradation at 16 weeks.

5. The coated tablet of claim 1, further comprising silicon dioxide.

* * * * *